United States Patent [19]
Kuroiwa et al.

[11] Patent Number: 5,719,030
[45] Date of Patent: Feb. 17, 1998

[54] MONOCLONAL ANTIBODY TO PROSTATE-DERIVED ACID PHOSPHATASE AND METHOD FOR DETERMINATION OF ACID PHOSPHATASE USING THE SAME AS WELL AS KIT FOR DETERMINATION

[75] Inventors: Katsumasa Kuroiwa; Katsuhiro Katayama; Takahiro Tomiyama; Toshihide Miura, all of Koriyama; Takeshi Nagasawa, Urawa, all of Japan

[73] Assignee: Nitto Boseki Co., Ltd., Fukushima, Japan

[21] Appl. No.: 380,243

[22] Filed: Jan. 26, 1995

Related U.S. Application Data

[62] Division of Ser. No. 224,172, Apr. 7, 1994, abandoned, which is a continuation of Ser. No. 909,110, Jul. 2, 1992, abandoned.

[30] Foreign Application Priority Data

Jul. 11, 1991 [JP] Japan ................................. 3-171192

[51] Int. Cl.$^6$ ............... G01N 33/53; C07K 16/00; C12P 21/08
[52] U.S. Cl. ............... 435/7.1; 435/7.23; 530/388.2; 530/388.26
[58] Field of Search .................. 435/7.1, 7.23; 530/388.2, 388.26

[56] References Cited

U.S. PATENT DOCUMENTS

| | | | |
|---|---|---|---|
| 4,474,893 | 10/1984 | Reading | 436/547 |
| 4,690,890 | 9/1987 | Loor et al. | 435/7 |

OTHER PUBLICATIONS

Lee et al. Ann. NY Acad Sci, 1982, 390: 52–61.
Gericke et al, Clin. Chem. 28: 596–602, 1982.
Kuciel et al, Biotech Appl Biochem, 1988, 10: 257–272.
Hoyhtya, Acta Universitatis Ouluensis A 1988, 203: 1–71.
Guding, Journal of Immunological Methods 39, pp. 285–308 (1980).
Needham, Journal of Immunological Methods, 99, pp. 283–284 (1987).
Ferrante et al., Clin. exp. Immunol. 39, pp. 532–537, (1980).
Ferrante et al., Journal of Immunological Methods, 48, pp. 81–85 (1982).
Allen H. Minor et al., Blood, 7, pp. 693–699 (1952).
Tullis, Blood, 7, pp. 891–896 (1952).
Golub, Immunology, A Synthesis, pp. 98–101, Sinauer Associates, Inc. Sunderland, Massachusetts, 1987.
Suzuki et al., Molecular and Cellular Probes 2, pp. 157–167 (1988).
Suzuki et al., Clinical Chemistry, vol. 36, No. 1 pp. 153–156 (1990).
Gerber et al., Clin Chem. vol. 33, No. 7, pp. 1158–1162 (1987).
Landt et al., Clin Chem. vol. 34, No. 3, pp. 575–581 (1988).
Panteghini et al., Clinical Biochemistry, vol. 23 pp. 1–4 (1990).
Choe et al., Ann NY Acad Sci vol. 390, pp. 16–36 (1982).
Hoyhtya et al., Clin Chem vol. 33(1) pp. 103–107 (1987).
Lillehoj et al., Molecular Immunology, vol. 19, No. 9, pp. 1199–1202 (1982).
Yamaura et al., Journal of Immunological Methods vol. 84. pp. 105–116 (1985).

*Primary Examiner*—Lila Feisee
*Assistant Examiner*—Susan Ungar
*Attorney, Agent, or Firm*—Darby & Darby

[57] ABSTRACT

According to the present invention, there are provided a monoclonal antibody to prostate-derived acid phosphatase and a method for determination of prostate-derived acid phosphatase using the monoclonal antibody. Prostate-derived acid phosphatase is boostered in animal and spleen cells isolated from the animal are fused with myeloma cells. The hybridoma capable of producing a monoclonal antibody having extremely high specificity to prostate-derived acid phosphatase is subjected to cloning. Using the monoclonal antibody produced by the hybridoma, prostate-derived acid phosphatase in a sample can be detected with extremely high sensitivity.

1 Claim, 2 Drawing Sheets

MONOCLONAL ANTIBODY TO PROSTATE-DERIVED ACID PHOSPHATASE AND METHOD FOR DETERMINATION OF ACID PHOSPHATASE USING THE SAME AS WELL AS KIT FOR DETERMINATION

This is a division of application Ser. No. 08/224,172 filed Apr. 7, 1994, now abandoned which is a continuation of Ser. No. 07/909,119 filed Jul. 2, 1992 now abandoned.

BACKGROUND OF THE INVENTION

1. Field of the Invention

The present invention relates a monoclonal antibody obtained using prostate-derived acid phosphatase as an antigen, a hybridoma capable of producing the monoclonal antibody, a kit for assaying prostate-derived acid phosphatase in a body fluid and a method for determination. According to the assay method using the monoclonal antibody of the present invention, the activity of prostate-derived acid phosphatase can be determined specifically with good sensitivity. Therefore the present invention is extremely useful for diagnosis of prostatic cancer.

2. Related Art Statement

Prostate-derived acid phosphatase (phosphomonoesterase EC3.1.3.2; hereafter referred to as PAP) is an enzyme that hydrolyzes a phosphoric acid monoester under acidic conditions (pH of 4 to 6). In patients with prostatic cancer, a marked increase of PAP level in body fluids is noted. For this reason, attention has been brought to determination of PAP as a tumor marker in clinical diagnosis.

The following methods for assaying the activity of PAP are known heretofore.

(1) Assay for PAP as Enzyme Activity (EA)

As shown below, methods for using various synthetic substrates are reported and some of them have been practically applied to ordinary clinical inspection. In all of these methods, tartaric acid is used to inhibit PAP and the residual activity of acid phosphatase is assayed; this activity is subtracted from the total activity of acid phosphatase to determine PAP activity.

(a) Method using β-glycerophosphate as substrate:

Hydrolysis of β-glycerophosphate by acid phosphatase gives glycerine and inorganic phosphorus. The inorganic phosphorus is allowed to produce a color and the color is measured [Bodansky, A.: J. Biol. Chem., 101, 93 (1933)].

(b) Method using p-nitrophenylphosphate as substrate:

Hydrolysis of p-nitrophenylphosphate by acid phosphatase gives p-nitrophenol, which is reacted with an alkali to form a color and the color is measured [Hudson, P. B.: J. Urol., 58, 89 (1947)].

(c) Method using phenylphosphate as substrate:

There is a method which comprises reacting the phenol formed by acid phosphatase-hydrolysis with Folin-Ciocalten reagent to form a color [King, E. J., Armstrong, A. R.: Canad. Med. Assoc. J., 31, 376 (1934)] and a method which comprises oxidatively condensing the resulting phenol with 4-aminoantipyrine and measuring the formed quinone of a red color [Kind, P. R. N., King, E. J.: J. Clin. Path., 7, 322 (1954)].

(d) Method using naphthylphosphate as substrate:

Naphthol formed by hydrolysis with acid phosphatase is reacted with Fast Red TR to form an azo dye and the azo dye is colorimetrically determined [Hillman, G.: Z. Klin. Chem., Klin. U. Biochem., 9, 237 1971)].

(e) Method using 2,6-dichloro-4-nitrophenylphosphate as substrate:

The yellow hue of 2,6-dichloro-4-nitrophenol formed by hydrolysis with acid phosphatase and is colorimetrically determined at 400 nm [Teshima, S., Hayashi, Y., Ando, M.: Clin. Chim. Acta, 168, 231 (1987)].

(f) Method using 2-chloro-4-nitrophenylphosphate as substrate:

The yellow hue of 2-chloro-4-nitrophenol formed by hydrolysis with acid phosphatase and is colorimetrically determined at 400 nm [K. Lorentz and K. Assel, Enzyme, 20, 248 (1975)].

(g) Method using 2,6-dichloro-4-acetylphenylphosphate as substrate:

The amount of 2,6-Dichloro-4-acetylphenol formed by hydrolysis with acid phosphatase is determined by measuring absorbance at 340 nm [Kuroiwa, K., Katayama, K., Miura, T., Japanese Patent KOKAI (Laid-Open) No. 2-180892].

(2) Method for Immunologically Assaying Acid Phosphatase Protein (IA)

(a) Radioimmunoassay (RIA):

Antibody (anti-PAP serum)-bound antigen (sample from a patient) is reacted with isotope-labeled PAP. Then the bound and unbound antibodies are separated from each other using a second antibody and PAP concentration in the patient's sample is counted by a gamma counter [Vihko, P., Clin. Chem., 24, 1915 (1978)].

(b) Enzymeimmunoassay (EIA):

PAP in a sample from a patient is captured by anti-PAP antibody and a second antibody is then added thereto. This second antibody is bound to peroxidase. Utilizing the peroxidase activity, a color is formed with ortho-phenylenediamine (OPD) and colorimetrically assayed [Choe, B. K., Clin. Chem., 26 (13), 1854 (1980)].

(c) Immunological enzyme assay:

Anti-PAP monoclonal antibody immobilized onto the inner surface of a polystyrene tube is reacted with a sample to trap aPAP as anti-PAP-monoclonal antibody-PAP complex on the surface of the tube; after washing other components off, PAP is reacted with substrate [KIKI/SHIYAKU (Device and Reagent), XIII: 1, 47–54 (1990); ibid., XIII: 4, 761–766 (1990)].

The known methods as mentioned above have problems to be solved as discussed in detail below.

(1) Problems Involved in Assaying PAP as Enzyme Activity (EA)

Acid phosphatase is present in prostate in an extremely large amount and widely distributed in almost all organs such as erythrocytes, bones, platelet, leukocytes, kidney, liver, etc.

In the aforesaid method as enzyme activity (EA), PAP is inhibited by tartaric acid. The pap activity is obtained by subtracting the total acid phosphatase activity seen in the presence of tartaric acid from the total activity seen without adding tartaric acid. Since its operations is simple and the reagents are available for a general-purpose automated analytical device, this method is used for ordinary clinical inspection. However, tartaric acid does not inhibit only PAP specifically but also inhibits acid phosphatase derived from platelet, leukocyte, kidney, liver and spleen. Therefore, PAP is not strictly assayed by this method. As stated above, the PAP activity level is obtained from the tartaric acid-sensitive fraction and hence, lacks specificity. As it is the case, this method is neither specific nor so significant clinically as a marker of prostatic cancer.

(2) Problems Involved in Immunologically Assaying Acid Phosphatase Protein (IA)

(a) In radioimmunoassay (RIA), special facilities are required because radioisotope is used. There is also a problem in management or control of such facilities. The method also requires about 2 days for performance of the assay.

(b) Enzymeimmunoassay (EIA) is not so restricted as noted with RIA because EIA does not use radioisotope and thus is widely used for ordinary clinical tests. However, it takes for 2 to 5 hours for assay, B/F (Bound/Free) separation is needed, operations are complicated, a large number of specimens cannot be processed and EIA does not fit a general purpose automated analytical device. In addition, the stability of EIA reagents such as substrate (OPD), etc. used in the detection system are poor.

(c) In immunological enzyme assay, the sensitivity and accuracy of the test are extremely high. However, some of the conventional methods still require complicated operations. It is also disadvantageous that the stability of Fast Red TR used in the detection system is poor.

SUMMARY OF THE INVENTION

The present inventors have made extensive investigations to solve the problems involved in the foregoing methods. As a result, it has been found that using PAP as an antigen, a novel monoclonal antibody which inhibits the activity of PAP in an extremely specific manner is prepared and by using the monoclonal antibody in the PAP assay system as a PAP activity inhibitor, the PAP activity can be assayed with extremely high sensitivity in a simple fashion. The present invention has thus been completed.

That is, a first object of the present invention is to provide a monoclonal antibody which specifically inhibits the enzyme activity of PAP.

A second object of the present invention is to provide a hybridoma capable of producing the monoclonal antibody described above.

A third object of the present invention is to provide a method for determination of the PAP activity characterized by using the monoclonal antibody described above as a PAP activity inhibitor.

A fourth object of the present invention is to provide a kit for assaying PAP activity comprising the monoclonal antibody described above as one of reagents.

These and other objects and advantages will be apparent from the following description.

A first aspect of the present invention is concerned with a novel monoclonal antibody which specifically inhibits the enzyme activity of prostate-derived acid phosphatase.

A second aspect of the present invention is concerned with a method for assaying PAP activity which comprises:

(i) reacting a sample with a substrate for acid phosphatase to determine the total acid phosphatase activity in the sample;

(ii) on the other hand, reacting a sample with the monoclonal antibody to inhibit the prostate-derived acid phosphatase activity in the sample and then determining non-prostate-derived acid phosphatase activity in the sample as in (i) above; and, (iii) subtracting the total non-prostate-derived acid phosphatase activity determined in (ii) above from the total acid phosphatase activity determined in (i) above.

A third aspect of the present invention is concerned with a kit for determination of prostate-derived acid phosphatase activity comprising the monoclonal antibody as one of reagents.

BRIEF DESCRIPTION OF THE DRAWINGS

FIG. 3 indicates relationship between the assay method of the present invention and EIA.

DETAILED DESCRIPTION OF THE INVENTION

Figure 1:
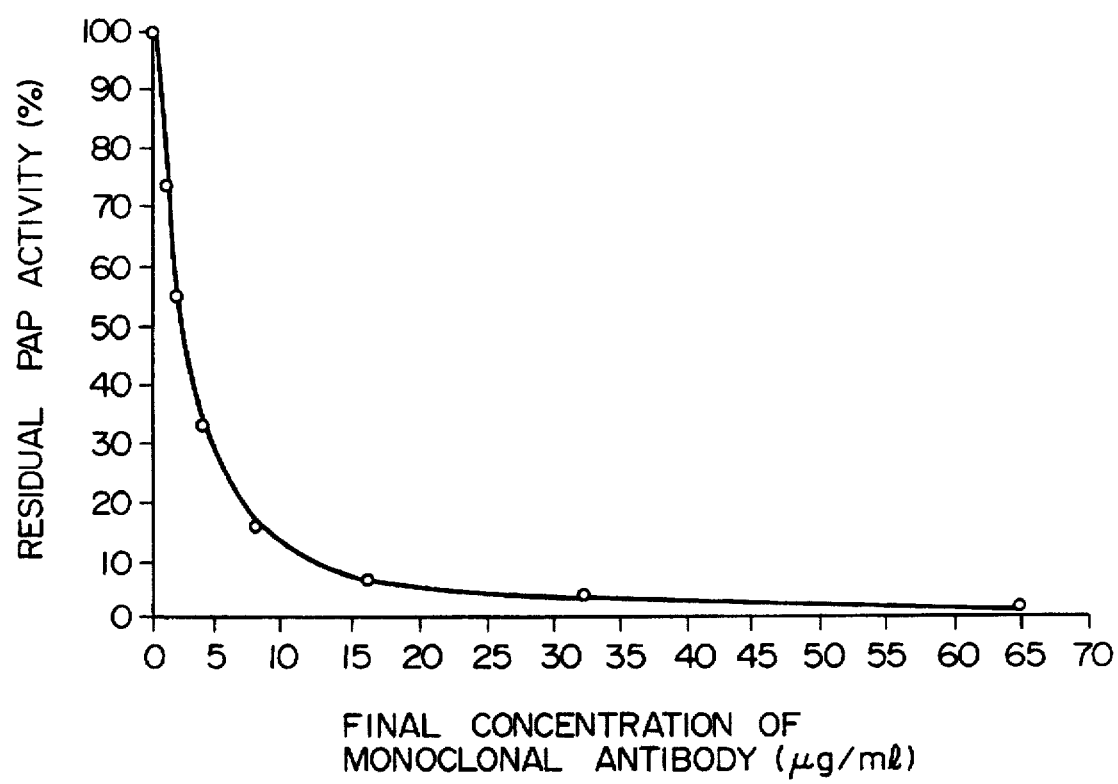
FIG. 1 shows the residual PAP activity (%) in the system where the monoclonal antibody is added, as a function of the final concentration of the monoclonal antibody.

Hereafter the present invention is described in detail.

The monoclonal antibody of the present invention has an extremely high specificity to PAP. More specifically, the monoclonal antibody of the present invention does not substantially react with any of acid phosphatase other than PAP, such as platelet-derived acid phosphatase, erythrocyte-derived acid phosphatase and leukocyte-derived acid phosphatase, etc., or shows cross reactivity of less than 5% with any acid phosphatase other than PAP. Accordingly, the monoclonal antibody of the present invention specifically binds to PAP and completely inhibits the PAP activity.

The monoclonal antibody of the present invention belongs to immunoglobulin class IgA and its L chain is κ chain.

The monoclonal antibody of the present invention can be obtained as follows.

An animal is immunized with, e.g., human-derived PAP and spleen cells obtained from the thus obtained immunized animal are fused with myeloma cells. A hybridoma capable of producing the desired monoclonal antibody is cloned and then the hybridoma is cultured and the produced monoclonal antibody is isolated. Thus, the monoclonal antibody of the present invention can be obtained.

Animals which are appropriate for immunization with PAP are rats or mice. More specifically, female Balb/c mice (Clea Japan Inc.) or mice of other strains, e.g., ICR, C3H, C57BL, DBA strain and Balb/c strain nude mice may also be used.

Booster and post-treatment may be performed in a conventional manner [Tatsuo Iwasaki, Tamie Ando, Kaoru Ichikawa and Kotaro Yasui: "Monoclonal Antibody" (Kodansha Publishing Co.)].

For booster and post-treatment, e.g., human PAP antigen [M. Derechim. Biochem. Biophys. Acta, 250, 143 (1971)] is intraperitoneally injected to mouse in intervals of 10 to 14 days and several days after the final injection of the antigen, spleen cells are withdrawn for cell fusion.

Myeloma cells are used for cell fusion, for example, P3-X63-Ag8-U1 cells [YeHon, D. et al., Current Topics in Microbiology and Immunology, 81 (1971)].

Spleen cells are fused with the myeloma cells using an appropriate fusion accelerator. A preferred ratio of spleen cells to myeloma cells is in a range of approximately from 20:1 to 2:1.

As a preferred fusion accelerator, for example, polyethylene glycol having an average molecular weight of 1000 to 4000 may be used advantageously but other fusion accelerators known in the art, e.g., Sendai virus may also be used.

The hybridomas obtained after cell fusion are cloned by limiting dilution. Cloning of the hybridomas is carried out by repeating the limiting dilution while verifying the presence or absence of anti-PAP antibody in the culture supernatant of fused cells by the method for assaying acid phosphatase activity using, e.g. using, 2,6-dichloro-4-acetylphenylphosphate as substrate [Japanese Patent KOKAI (Laid-Open) No. 2-180892].

According to the present invention, one representative hybridoma is established; this hybridoma PAP-D11 was internationally deposited in Fermentation Research Institute of the Agency of Industrial Science & Technology of Japan on Jun. 20, 1991 under Budapest Treaty and is given FERM BP-3461.

To obtain the desired monoclonal antibody from hybridomas, the following process may apply. For example, a hybridoma is cultured in an appropriate medium for a definite period of time and the monoclonal antibody produced by the hybridoma. Another process comprises intravenously injecting the hybridoma to, e.g., mouse having a homo gene or semi-homo gene and collecting the monoclonal antibody produced by the hybridoma from blood and ascites of this host animal in a definite period of time after the injection.

The monoclonal antibody of the present invention thus obtained reacts specifically with PAP and can inhibit the PAP activity substantially completely.

Therefore, using this monoclonal antibody as a PAP activity inhibitor, the PAP activity in a sample can be assayed with high sensitivity. More specifically, the PAP activity in a sample can be assayed by the following procedures with an extremely high sensitivity in a simple manner.

That is, the PAP activity can be assayed by:

(i) reacting a sample with a substrate for acid phosphatase to determine the total acid phosphatase activity in the sample;

(ii) on the other hand, reacting a sample with the monoclonal antibody to inhibit the prostate-derived acid phosphatase activity in the sample and then determining non-prostate-derived acid phosphatase activity in the sample as in (i) above; and, (iii) subtracting the total non-prostate-derived acid phosphatase activity determined in (ii) above from the total acid phosphatase activity determined in (i) above.

As a sample, a representative example is serum collected from the patient which is suspected to suffer from prostatic cancer.

Examples of the substrate for acid phosphatase include p-nitrophenylphosphate, phenylphosphate, naphthylphosphate, 2,6-dichloro-4-nitrophenylphosphate, 2-chloro-4-nitrophenylphosphate, 2,6-dichloro-4-acetylphenylphosphate, etc. Among them, 2,6-dichloro-4-acetylphenylphosphate is particularly advantageous because of its highest sensitivity.

By adding these substrates to a sample, the substrates are hydrolyzed by acid phosphatase in the sample to liberate the corresponding phenol derivatives or inorganic phosphorus. The phenol derivatives or inorganic phosphorus are directly colorimetrically measured. Alternatively, the phenol derivatives or inorganic phosphorus may be reacted with a color forming reagent directly or indirectly and the resulting color is colorimetrically measured. Thus, the total acid phosphatase activity or non-prostate-derived acid phosphatase activity in the sample can be determined.

At the step (ii) described above, the sample is generally mixed with the monoclonal antibody, the mixture is previously heated and then the substrate is added to the mixture. A time period for the previous heating may vary depending upon the activity of the monoclonal antibody used but generally for 1 to 10 minutes, preferably for 5 minutes.

The kit for determination of PAP activity in accordance with the present invention used in the assay method described above comprises at least the monoclonal antibody of the present invention as one of reagents.

In addition to the monoclonal antibody, the kit may contain, for example, substrate for acid phosphatase, a color forming reagent system for measuring the hydrolysate of the substrate, buffer solutions used for the assay, etc., as one reagent component of the kit.

EXAMPLE 1

Preparation of Monoclonal Antibody (1) Booster

Following the method of Tatsuo Iwasaki et al. described in "Monoclonal Antibody" published by Kodansha Publishing Co., mouse was boostered. After 200 µg of human PAP (Sigma Co., Phosphatase Acid Blostatic Lot. 89H7822) was blended with 1 ml of Freund's complete adjuvant (FCA), the mixture was made water-in-oil emulsion to prepare antigen-FCA emulsion. Using Balb/cA mouse of 6 week age, 200 µl (corresponding to 20 µg of PAP) of the antigen-FCA emulsion was intraperitoneally given to the mouse as a first booster. As a second booster and so on, 100 µl (corresponding to 10 µg of PAP) of antigen-Freund's incomplete adjuvant (FICA) emulsion was intraperitoneally given in 2 weeks interval from the first booster. The final booster was performed by intraperitoneally administering 200 µl (corresponding to 20 µg of PAP) of antigen-FICA emulsion to the mouse with passage of 8 weeks after the first booster.

(2) Cell Fusion

Following the method of Kohler, G. and Milstein, Nature, 256, 405 (1975), cell fusion was performed.

Three to four days after the final booster, $1\times10^7$ counts of spleen cells were fused with $1\times10^8$ of P3-X63-Ag8-U1 cells using 50% polyethylene glycol 4000 [Littlefield, J. W., Science, 145, 709 (1964)]. The fused cells were separately charged in a 96-well plate and cultured at 37° C. in HAT medium (RPMI-1640 medium [G. E. Moore, A. A. Sandberg and K. Ulrich, J. Nat. Cancer Inst., 36, 405 (1966)] supplemented with hypoxanthine, aminopterin and thymidine and containing 10% fetal calf serum) under 5% $CO_2$.

(3) Screening of Antibody

Regarding the wells where proliferation of hybridomas was noted, the presence or absence of anti-PAP antibody in the culture supernatant was examined by the method for assaying acid phosphatase activity using 2,6-dichloro-4-acetylphenylphosphate as substrate. After 100 µl of the culture supernatant was combined with 100 µl of PAP (corresponding to 20 IU/liter), the mixture was allowed to stand at 37° C. for an hour. Then, the acid phosphatase activity was determined using an automated analytical device, Hitachi Model 7150 by the method described in Japanese Patent KOKAI (Laid-Open) No. 2-180892 using as substrate 2,6-dichloro-4-acetylphenylphosphate. As control, the system in which 0.1M citrate buffer (pH 5.4, 25° C.) was added instead of the culture supernatant was used. Where the activity was reduced by 10% or more than the control, it was judged that the antibody production was positive.

(4) Cloning

Following the method described in J. W. Goding, J. Immunol. Methods, 39, 285 (1980), cloning was performed.

The hybridomas which were noted to produce the antibody in the culture supernatant were subjected to cloning 4 times by limiting dilution using RPMI 1640 medium as a diluting solution. The monocloned hybridoma was again assayed by the procedure (3) described above and the monoclonal antibody-producing hybridoma was established. The thus obtained hybridoma PAP-D11 was internationally deposited in Fermentation Research Institute of the Agency of Industrial Science & Technology of Japan on Jun. 20, 1991 under Budapest Treaty and is given FERM BP-3461.

(5) Production and Purification of Monoclonal Antibody

The monoclonal antibody-producing hybridoma PAP-D11 was proliferated in Petri dish. Then, the hybridoma was intraperitoneally transplanted to Balb/c mouse pretreated with Pristane (Aldrich Co., Ltd.). The monoclonal antibody was purified by subjecting the mouse ascites obtained to salting-out with 50% ammonium sulfate and chromatography with 20 mM Tris buffer (pH 8.0) (gradient elution in NaCl concentration of 50 to 300 mM) using DEAE SEPHAROSE CL-6B column (manufactured by Pharmacia Fine Chemicals, Inc.).

(6) Property of Monoclonal Antibody

Globulin subclass of the monoclonal antibody was determined by EIA using rabbit anti-mouse immunoglobulin (IgG1, G2a, G2b, G3, IgM, IgA, κ, λ) (Zymet Co., Ltd.) and goat anti-rabbit antibody labeled with peroxidase (POD) (Zymet Co., Ltd.). The result reveals that the monoclonal antibody of the present invention belongs to immunoglobulin class IgA and its L chain is κ chain.

EXAMPLE 2

Determination of PAP Activity Reagents (A) Buffer: 0.1M citrate, 0.5% bovine serum albumin, pH 5.4

(B) Substrate solution: 2,6-dichloro-4-acetylphenylphosphate (7.8 mM)

(C) Buffer solution containing monoclonal antibody:

containing 320 μg/ml of monoclonal antibody of buffer solution (A)

(D) Sample: human prostate-derived acid phosphatase (Sigma Co.)

(1) Determination of total acid phosphatase activity

To 2.0 ml of the buffer solution (A) is added 0.1 ml of a sample. The mixture is previously warmed at about 37° C. for 2 to 5 minutes and 0.5 ml of the substrate solution (B) is added thereto. At the same time, a stop watch starts and absorbance at 340 nm is measured accurately 1 and 2 minutes after. A change in absorbance per minute is thus determined. The acid phosphatase activity is calculated by the following equation:

$$IU/\ell = \frac{\Delta OD/min^{1)} \times \text{total amount of reaction solution}}{\text{molecular extinction coefficient}^{2)} \times \text{amount of sample}} \times 10^4$$

[1] ΔOD/min means a change in absorbance per minute at the measurement wavelength of 340 nm.
[2] Molecular extinction coefficient of 2,6-dichloro-4-acetylphenol at the wavelength of 340 nm is 21500.

(2) Determination of non-prostate-derived acid phosphatase activity

To 2.0 ml of the buffer solution (C) is added 0.1 ml of the same sample as in (1). The mixture is previously warmed at about 37° C. for 2 to 5 minutes and 0.5 ml of the substrate solution (B) is added thereto. At the same time, a stop watch starts and absorbance at 340 nm is measured accurately 1 and 2 minutes after. A change in absorbance per minute is thus determined. The non-prostate-derived acid phosphatase activity is calculated by the equation described above. PAP activity is determined by subtracting the activity level of (2) from that obtained in (1).

FIG. 1 shows the residual PAP activity (%) in the system where the monoclonal antibody is added, as a function of the final concentration of the monoclonal antibody. The results indicate that PAP is sufficiently inhibited.

Figure 2:
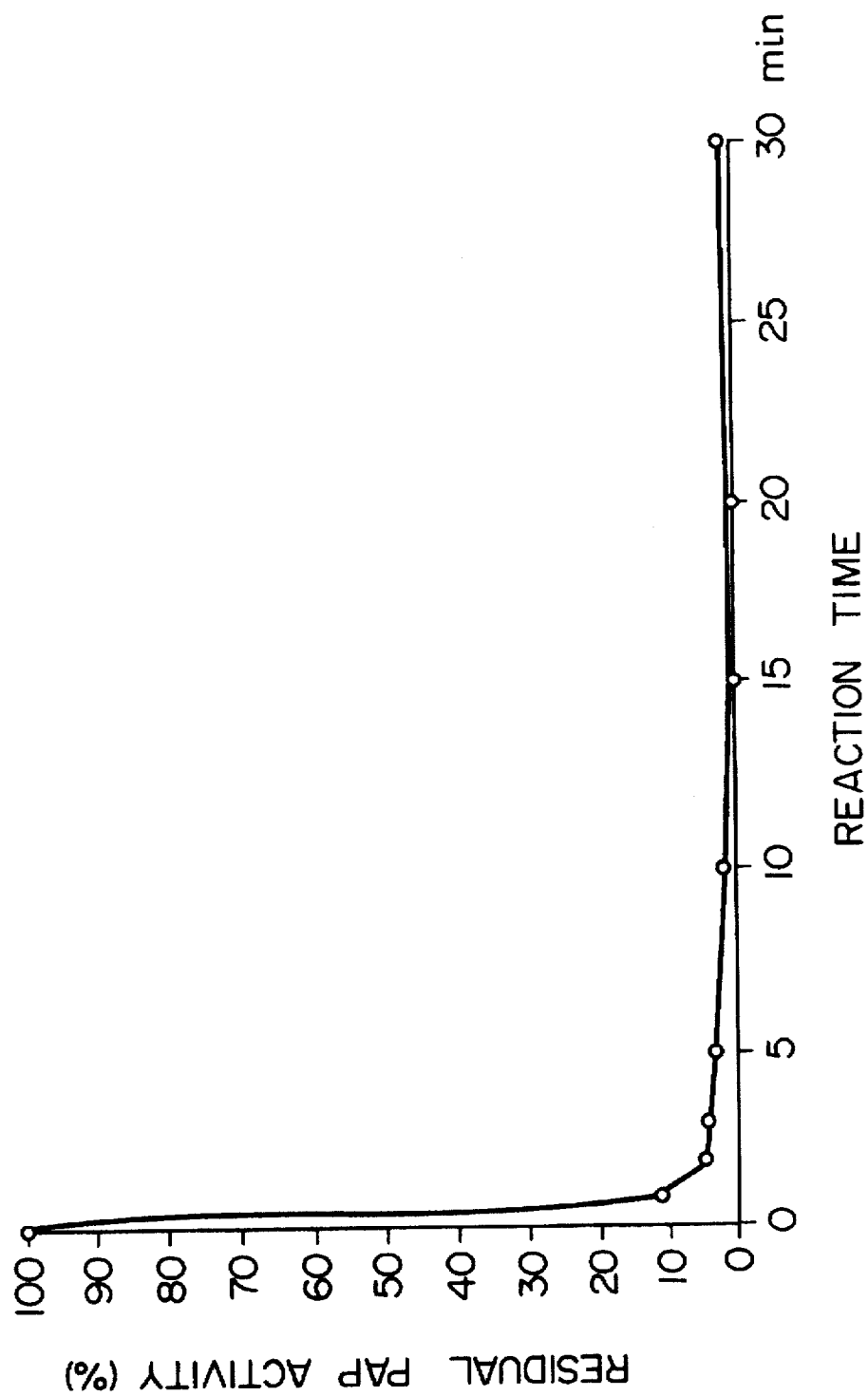
FIG. 2 shows the residual PAP activity (%) in the system where the monoclonal antibody is added, as a function of reaction time with the monoclonal antibody.

FIG. 2 shows the residual PAP activity (%) in the system where the monoclonal antibody is added, as a function of reaction time with the monoclonal antibody. The results indicate that PAP can be inhibited in a short period of time, showing applicability to a general purpose automated analytical device.

FIG. 3 indicates relationship between activity level of 39 samples from patients obtained using the reagent and assay method (Y) of the present invention in an automated analytical device of Hitachi Model 7150 and an amount of protein measured by EIA (X), wherein correlation coefficient was 0.997 and regression equation was: Y=0.4443X−0.143. This means extremely good correlation to conventional EIA, suggesting usefulness in clinical test.

EXAMPLE 3

Determination of Cross Reactivity of Monoclonal Antibody

Samples containing various blood cells were isolated from human blood according to the method described in Yoshihiro Kinoshita: Method for Isolation of Blood Cells "Series of Clinical Test Technology 3, Blood Test", 416–447 (1972). The isolated blood cells were frozen and thawed 4 to 5 times and centrifuged. The thus obtained supernatant was used for determination.

Using the same reagents as used in Example 2, cross reactivity was examined following the procedure of Example 2.

At the same time, similar determination was performed using tartaric acid. Determination was performed in a manner similar to Example 2, except for using buffer containing 26 mM tartaric acid instead of the buffer solution containing monoclonal antibody as reagent (C) of Example 2. The results are shown in Table 1.

TABLE 1

| Method | Cross Reactivity (%) Various Acid Phosphatase | | |
|---|---|---|---|
| | Derived from Platelet | Derived from Leucocyte | Derived from Erythrocyte |
| Method of Example 2 | 0 | 5 | 0 |
| Method using tartaric acid | 9 | 27 | 0 |

The characteristics and advantages of the monoclonal antibody of the present invention, and the method and kit for assaying PAP activity using the same are clearly shown by FIGS. 1 through 3 appended and Table 1.

FIG. 1 shows the residual PAP activity (%) in the system where the monoclonal antibody is added, as a function of the final concentration of the monoclonal antibody. The results indicate that PAP is sufficiently inhibited.

FIG. 2 shows the residual PAP activity (%) in the system where the monoclonal antibody is added, as a function of reaction time with the monoclonal antibody. The results indicate that PAP can be inhibited in a short period of time, showing applicability to a general purpose automated analytical device.

FIG. 3 indicates relationship between the activity level obtained using the method and kit for determination of the present invention and an amount of protein measured by EIA. The method of the present invention extremely well correlates to conventional EIA, suggesting usefulness in clinical test.

Table 1 shows cross reactivity (%) with acid phosphatase in blood other than PAP, indicating high specificity of the monoclonal antibody of the present invention.

As shown above, the present invention enables to determine PAP activity in a sample in a simple and rapid manner with extreme accuracy and hence markedly improves clinical diagnosis.

What is claimed is:

1. A method for assaying prostate-derived acid phosphatase activity in a sample, which comprises:

(i) reacting a first aliquot of said sample with a substrate for acid phosphatase to determine the total acid phosphatase activity in the sample;

(ii) reacting a second aliquot of said sample with a monoclonal antibody produced from a hybridoma having a deposit number of FERM BP-3461 to specifically inhibit the prostate-derived acid phosphatase activity in said second aliquot, and then reacting said second aliquot with a substrate to determine non-prostate-derived acid phosphatase activity in the sample; and (iii) determining the prostate-derived acid phosphatase activity by subtracting the total non-prostate-derived acid phosphatase activity determined in (ii) above from the total acid phosphatase activity determined in (i) above.

* * * * *